United States Patent
Pitt et al.

(10) Patent No.: US 7,282,362 B2
(45) Date of Patent: Oct. 16, 2007

(54) TRAY WITH PROTRUSIONS

(75) Inventors: Aldo Pitt, Wayland, MA (US); Donald Rising, Stow, MA (US); Kenneth DeSilets, Westford, MA (US)

(73) Assignee: Millipore Corporation, Billerica, MA (US)

( * ) Notice: Subject to any disclaimer, the term of this patent is extended or adjusted under 35 U.S.C. 154(b) by 166 days.

(21) Appl. No.: 10/166,802

(22) Filed: Jun. 11, 2002

(65) Prior Publication Data

US 2002/0192811 A1 Dec. 19, 2002

Related U.S. Application Data

(60) Provisional application No. 60/298,265, filed on Jun. 14, 2001.

(51) Int. Cl.
*C12M 1/34* (2006.01)
*C12M 1/12* (2006.01)

(52) U.S. Cl. .............. 435/288.4; 135/297.5; 422/101; 422/102; 73/64.47; 210/321.84

(58) Field of Classification Search ............ 435/288.4, 435/297.2, 297.1, 297.5, 305.2, 305.3; 422/101, 422/102; 73/38, 64.47; 210/321.84, 406
See application file for complete search history.

(56) References Cited

U.S. PATENT DOCUMENTS

| | | | |
|---|---|---|---|
| 4,204,045 A | | 5/1980 | Kjellander et al. |
| 4,787,988 A | * | 11/1988 | Bertoncini et al. ......... 210/808 |
| 4,927,604 A | * | 5/1990 | Mathus et al. .............. 422/101 |
| 5,009,780 A | * | 4/1991 | Sarrasin ...................... 210/238 |
| 5,141,718 A | | 8/1992 | Clark |
| 5,462,874 A | | 10/1995 | Wolf et al. |
| 5,534,227 A | | 7/1996 | Lahm et al. |
| 5,603,899 A | * | 2/1997 | Franciskovich et al. .... 422/100 |
| 5,624,815 A | * | 4/1997 | Grant et al. .................. 435/30 |
| 5,650,323 A | | 7/1997 | Root |
| 5,795,775 A | | 8/1998 | Lahm et al. |
| 5,801,055 A | | 9/1998 | Henderson |
| 5,837,198 A | | 11/1998 | Itani |
| 5,972,694 A | | 10/1999 | Mathus |

(Continued)

FOREIGN PATENT DOCUMENTS

EP 0 418 035 A1 3/1991

(Continued)

OTHER PUBLICATIONS

"Selection of Invasive and Metastatic Subpopulations from a Heterogeneous Human Melanoma Cell Line", BioTechniques, Vo. 9, No. 3 (1990), p. 324.

(Continued)

*Primary Examiner*—William H. Beisner

(57) ABSTRACT

A feeding tray for retaining a liquid nutrient liquid is provided for use with a multiwell filter plate. The feeding tray includes a flat support surface surrounded by walls which retain liquid on the support surface. The flat support surface includes protrusions positioned to contact the membrane portion of a multiplicity of wells of the multiwell filter plate when the multiwell filter plate is removed from the feeding tray. These protrusions remove residual liquids from the bottom of each filter well thereby minimizing cross contamination in subsequent processing steps. Additionally, it may contain one or more baffles, in lieu of or in addition to the protrusions for controlling liquid movement during handling.

2 Claims, 7 Drawing Sheets

U.S. PATENT DOCUMENTS 6,893,562 B2 * 5/2005 Busnach et al. ............ 210/248

FOREIGN PATENT DOCUMENTS

| EP | 1 151 794 A2 | 7/2001 |
| WO | WO 99/21958 | 5/1999 |

OTHER PUBLICATIONS

1. Photograph of top plate of Multi-Screen Dual Access plate prototype, publicly provided by Millipore Corporation in Feb. 1993.
2. Photograph of three piece MultiScreen Dual Access Cell Culture System prototype, publicly provided by Millipore Corporation in Feb. 1993.

* cited by examiner

TRAY WITH PROTRUSIONS

This application claims benefit of U.S. Provisional Application No. 60/298,265, filed Jun. 14, 2001.

BACKGROUND OF THE INVENTION

This invention relates to a feeding tray for housing a nutrient medium utilized with a multiwell test apparatus suitable for promoting fluid interactions such as by growing cells in a nutrient liquid within a multiplicity of wells. More particularly, this invention relates to such a feeding tray of a multiwell test apparatus which permits adding or removing liquid from the feeding tray of the multiwell test plate without disturbing a material in the test plate such as cells within the wells.

At the present time, multiwell test apparatus for testing samples include a multiwell filter plate, a feeding tray, a multiwell receiver plate and a lid. The wells of the filter plate are formed of hollow members, typically tubular in shape although rectangular, square, triangular and hexagonal shapes have been used, with two open ends to one of which, typically the bottom one, is attached a membrane such as a microporous membrane. The members can be inserted into a feeding tray containing a nutrient medium so that cells in the wells can be attached to the membrane and grown thereon. The cells are fed as nutrients pass from the nutrient medium through the membrane and to the cells at a rate controlled by the concentration gradient of nutrients from the medium to the cells. The nutrient medium in the feeding tray is periodically replenished to maintain cell growth. It is desirable to effect replenishment of the nutrient medium quickly and in a manner that avoids damage to the membranes and the cells.

After the desired level of cell growth on the membranes of the wells has been attained, the multiwell filter plate can be utilized in conventional assay methods. These assay methods generally are effected by positioning the membranes and cells on the multiwell filter plate into the wells of the multiwell receiver plate, such as a 96 well receiver plate positioned below the multiwell filter plate or it just has to have the same number of wells in register with the cell/filter plate. The wells of the multiwell receiver plate contain a liquid composition to be assayed. The composition to be assayed diffuses into the cells if present and then through the membrane. The resultant liquid products within the wells of the multiwell filter plate or in the wells of the multiwell receiver plate then is assayed to determine the capability of the composition being assayed to permeate the cell barrier.

An important component in the drug discovery and development process is the determination of the oral absorption and bioavailability of new compounds. In order to perform this evaluation in a cost effective, high throughput and sensitive assay, it is ideal to use an in vitro device with a multitude of wells containing cells, a small amount of assay material and automation. Classically, the determination of in vitro oral absorption characteristics is performed using a defined epithelium cell line and measuring the apparent transport rate of the drug across a monolayer of the cells. More recently it is possible to rank/order the passive transport rate of potential drug candidates using an artificial membrane barrier. The values generated from these in vitro experiments are valuable methods for screening the most likely successful drug candidates long before the oral absorption rate are validated by in vivo measurements. A typical experiment for determining the drug absorption characteristics of a known or unknown chemical compound is performed as follows. The multiwell device is seeded with epithelium cells on top of the filter in a defined nutrients medium. The same medium is also added to the single well feeding tray, located below and in fluid contact with the device containing the cells. The cells are allowed to proliferate and differentiate over a number of days. The nutrient medium is periodically replaced with fresh medium to replenish exhausted nutrients and remove waste and dead cells. At the end of a growing time, the cells and multiwell device are gently washed with an isotonic buffer to remove protein and residual nutrient medium. At this time, the multiwell filter plate is transferred to the multiwell receiver plate and the chemicals to be assayed are introduced to either the compartment above the cell layer or below the cells and filter support in the multiwell receiver tray. The opposing chamber is filled with drug free buffer and the multiwell device is incubated for some period of time, typically at 37 degrees Centigrade with shaking. If multiple time points are desired, sampling from either compartment can be achieved without separating the device. The amount of drug/chemical that is transported across the cell barrier can be determined by a variety of analytical methods, but typically is determined using LC-MS/MS (Liquid Chromatography—Mass Spectrometry—Mass Spectrometry).

After the cells have been satisfactorily grown and the feeding tray is to be replaced by the multiwell receiver plate, it is desirable to minimize transport of the nutrient medium to the multiwell receiver plate thereby to minimize dilution of the composition being assayed. Thus, it is desirable to remove any droplets of nutrient medium retained on the lower surfaces of the membranes after the multiwell filter is removed from the nutrient medium in the feeding tray.

Accordingly, it would be desirable to provide a multiwell test apparatus which is capable of minimizing transport of nutrient medium to be mixed with a liquid composition to be assayed.

SUMMARY OF THE INVENTION

This invention will be described herein with reference to the growing and use of cells on a membrane positioned and secured to the bottom of each well of a multiwell filter plate. However, it is to be understood that the present invention need not be used in conjunction with cells. Other representative uses include filtration, dialysis, or the like.

The present invention provides a feeding tray for holding a nutrient which can be liquid or gel for use in a multiwell test apparatus. The feeding tray contains a nutrient medium on the flat support surface surrounded by walls which retain the nutrient medium.

The feeding tray includes a plurality of protrusions such as posts secured to and extending from the flat bottom surface, one protrusion positioned adjacent each well which extends into the feeding tray. A guide means is provided for positioning the wells so that pendant droplets can contact a protrusion as the multiwell filter plate is removed from the feeding tray so that any liquid droplet extending from the bottom surface of the membrane is guided by the protrusion back into the feeding tray. Thus, the protrusions provide a means for removing any excess liquid from the membranes which would dilute a liquid solution in wells of a multiwell receiver plate subsequently utilized in conjunction with the multiwell filter plate removed from the feeding tray. In addition, the presence of protrusions reduces the volume of nutrient medium needed to immerse the membranes.

In another embodiment, the use of one or more baffles, either formed as part of the bottom of the feed tray or formed separately and freely sitting in the feed tray may be used to control the movement or sloshing of the liquid in the tray during handling.

DESCRIPTION OF SPECIFIC EMBODIMENTS

Figure 1:
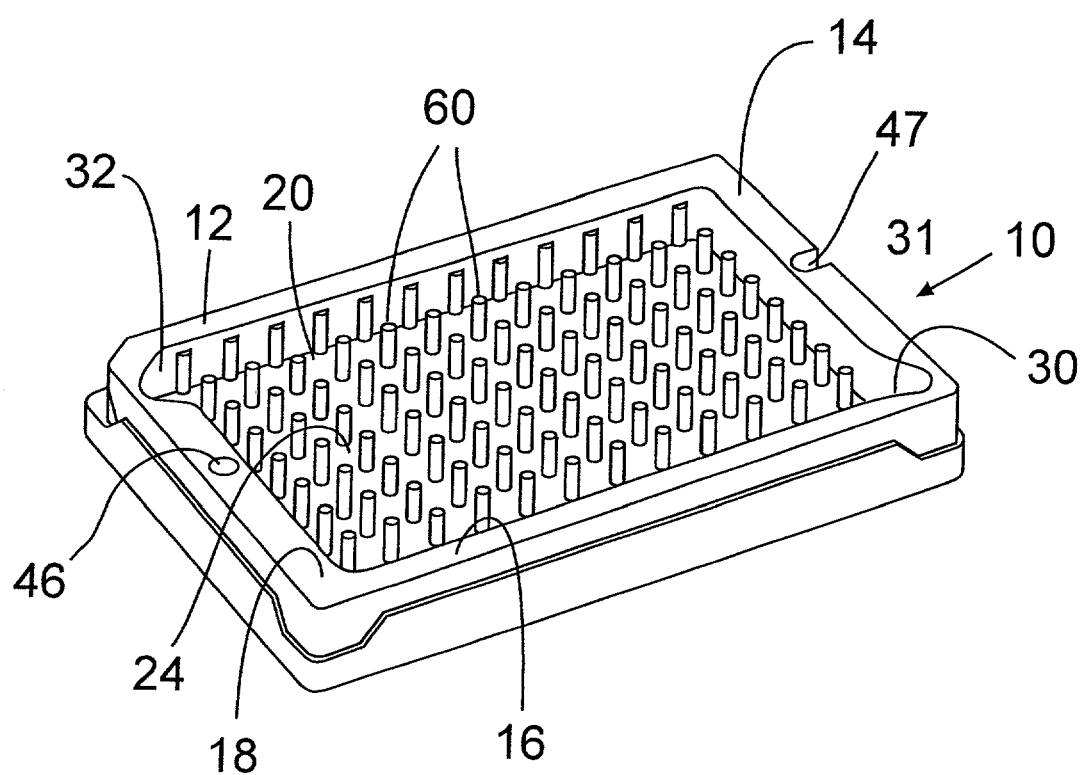
FIG. 1 is a top perspective view of the feeding tray of this invention.

While the present invention is described with reference to effecting cell growth and transport studies in a multiplicity of wells, it is to be understood that the present invention is applicable to manipulations involving, other sample processing for example, dialysis or diffusional studies, Referring to FIG. 1, the feeding tray 10 of this invention includes walls 12, 14, 16 and 18 and support surface 20 to house a nutrient medium. The support surface 20 includes protrusions 60 such as posts or ½ posts on wall 12 edge. Other shaped protrusions may be used provided they provide the same function and may include cones, dimples pyramids and the like. Liquid can be introduced into liquid introduction area 32 and can be removed from drain area 30. Feeding tray 10 also can be provided with recesses 46 and 47 into which alignment posts of a multiwell filter plate can fit.

Figure 2A:
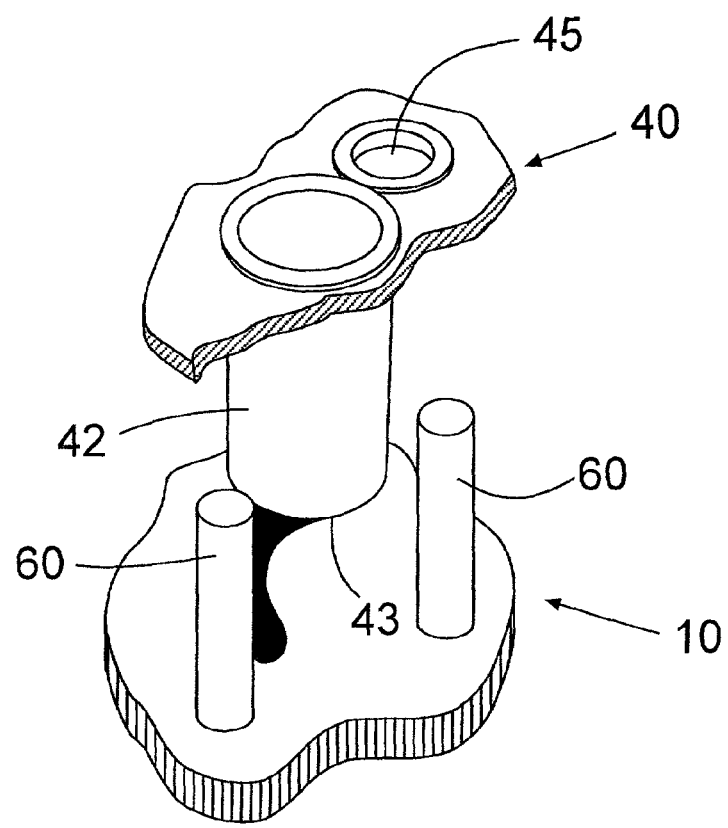
FIG. 2A is a partial perspective view of the feeding tray of this invention of a well of a multiwell filter plate.
Figure 2B:
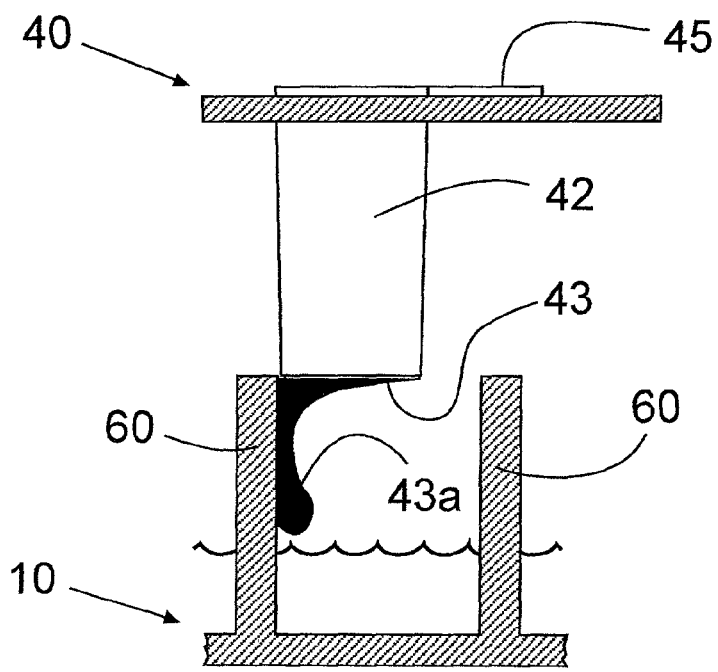
FIG. 2B is a partial cross-sectional view of the feeding tray of FIG. 2A.

The use of feeding tray 10 is exemplified with reference to FIGS. 2A and 2B. As shown in FIGS. 2A and 2B, the feeding tray 10 is positioned below multiwell filter plate 40 which includes a multiplicity of wells 42, such as 96 wells. A permeable barrier, typically one that is permeable to liquids and gases but not particles, such as a porous membrane, 43 is secured to the bottom of each of the wells 42. In use, the feeding tray 10 is provided with a depth of nutrient medium such that the membranes 43 of the wells 42 are immersed in the nutrient medium. Upon completion of a cell feeding cycle wherein cells are positioned on the top surface of membranes 43, the multiwell filter plate 40 is lifted away from feeding tray 10 and is moved so that wells 42 contact posts 60 so that excess liquid nutrient medium 43a flows down posts 60 and into feeding tray 10. Thus, nutrient medium is preserved.

Figure 2C:
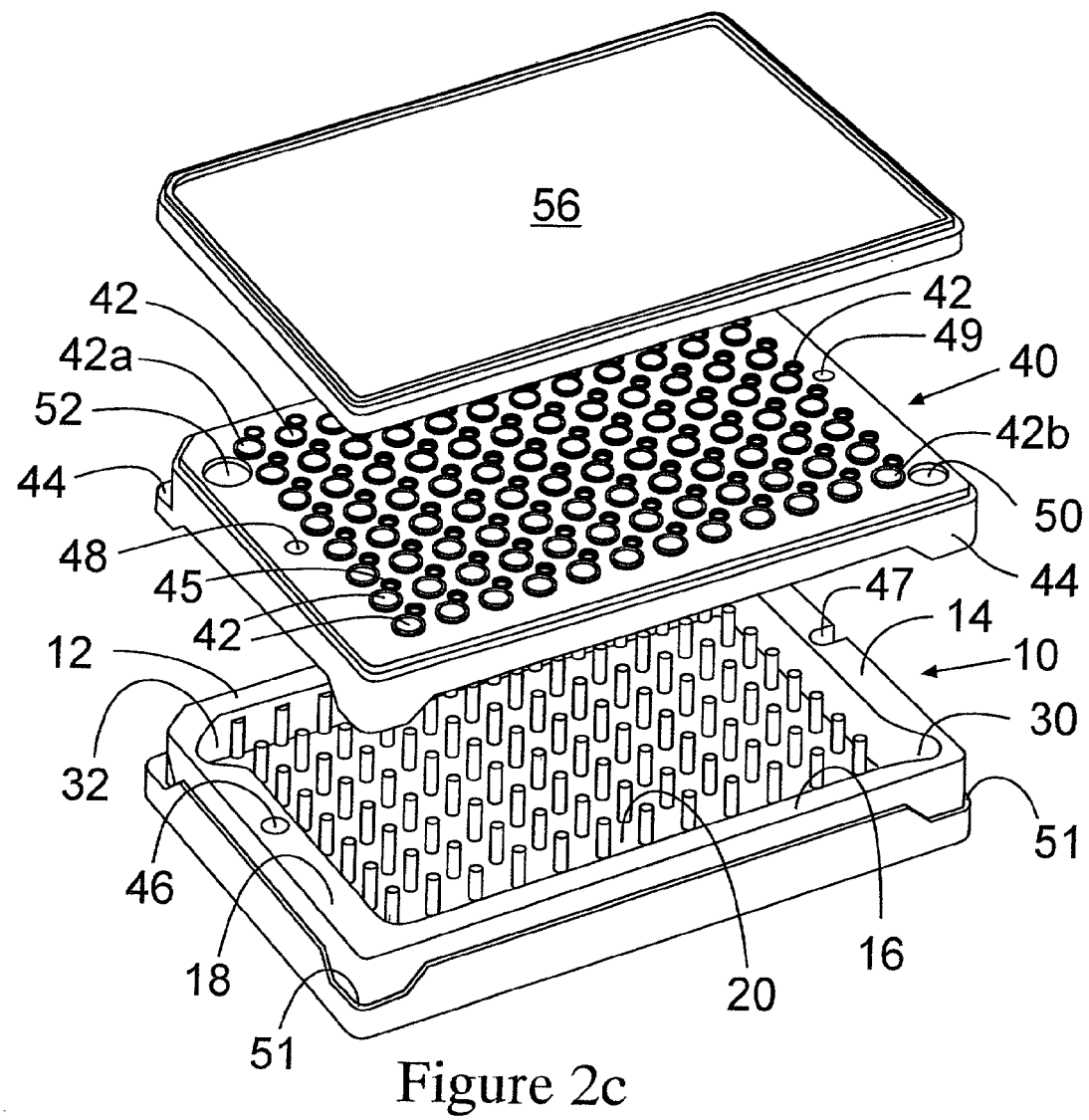
FIG. 2C shows a multiwell test apparatus including the feeding tray of this invention.

As shown in FIG. 2C, the multiwell filter plate 40 is provided with a plurality of wells 42. Each of the wells 42 has associated therewith an access hole 45 which permits access to a well of a multiwell receiver plate (not shown) which replaces the feeding tray during a sample assay step. The multiwell filter plate 40 can be provided with four legs 44 which fit into recesses 51 of feeding tray 10 thereby to provide mechanical stability of multiwell filter plate 40. The legs 44 also serve to position the membranes 43 to avoid contact with support surface 20 thereby to promote contact of liquid with the membranes 43. Feeding tray 10 also is provided with recesses 46 and 47 into which posts 48 and 49 fit. The posts 48 and 49 are asymmetrically positioned on feeding tray 10 so that well 42a is always positioned at the top left position of the well array and so that well 42b is always positioned at the lower right position of the well array. This position assures that a well always can be correctly identified according to its position. The posts 48 and 49 also position wells 42 of multiwell filter plate 40 at desired positions. Nutrient medium can be replenished through opening 52 in multiwell filter tray 40. The nutrient medium can be drained from feeding tray 10 through opening 50. Replenishment and drainage can be effected with liquid handling device such as a syringe, cannula, pipette or the like. Alternatively, drainage and replenishment can be effected simultaneously without the need to move multiwell filter tray 40 relative to feeding tray 10. Removable lid 56 is utilized to maintain sterility within wells 42 and to minimize evaporation of the nutrient medium. While FIGS. 2A and B shows one well 42 associated with each post 60, it should be understood that each post 60 could serve as many as four wells 42 if filter plate 40 is moved laterally in more than one direction.

Figure 3:
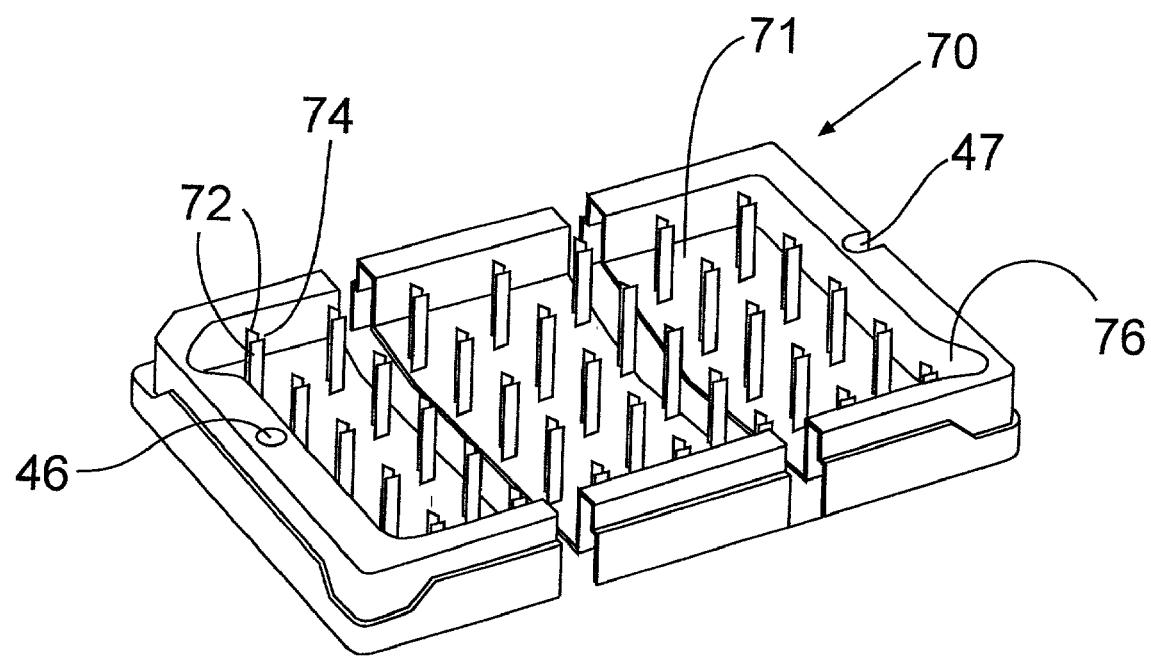
FIG. 3 is a top perspective view of an alternative feeding tray embodiment of this invention.

Referring to FIG. 3, the posts 60 of the feeding tray of FIGS. 1 and 2 are replaced in feeding tray 70 with guide wall protrusions 72 which are positioned to contact the membranes 43 at the bottom of the wells 42 in the manner set forth above with reference to FIGS. 2A and 2B. The protrusions 72 include openings 74 which direct liquid to drainage area 76 from which liquid can be removed with a conventional syringe, cannula, pipette or similar means.

Figure 4:
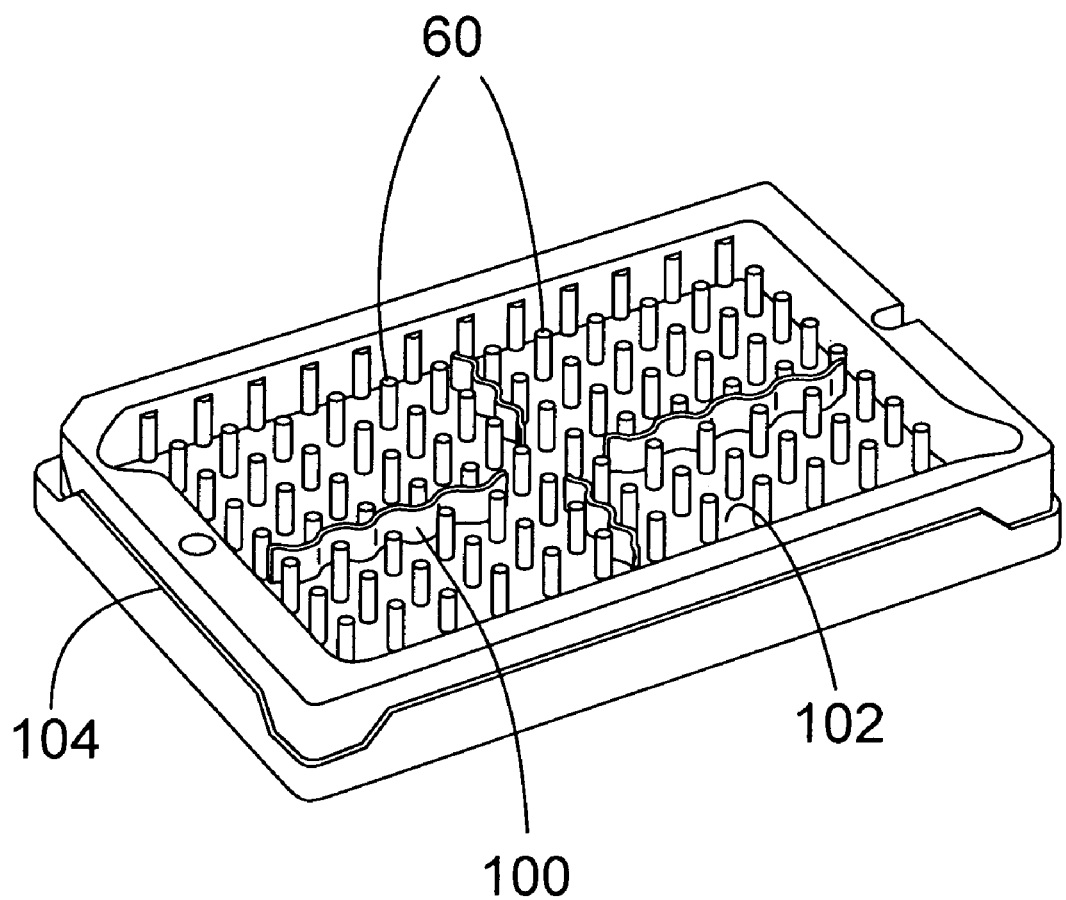
FIG. 4 is a perspective view of an alternative feeding tray embodiment of this invention.

In a further alternative embodiment of the present invention, one may use one or more baffles to reduce the movement or sloshing of the liquid in the feed tray, especially during handling, by humans or robotic equipment. FIG. 4 shows one such embodiment.

In this embodiment, the use of four baffles 100 is shown. The baffles 100 are attached to the bottom 102 of the feed tray 104. Preferably they are formed as part of the feed tray 104 such as by injection molding along with the tray when it is made although they may added as a separate element that is either attached to the tray sides or bottom or allowed to rest freely on the bottom of the tray. As shown, the baffles are arranged in a cross-like pattern and are separate and distinct from each other. As shown, they are also each formed in a repetitive "S" or wavy pattern. Alternatively, the baffle(s) 100 maybe straight or curvilinear or crossed (X-like elements) or the like so long as they are able to perform their function while allowing the multiwell filter plate (not shown) to fit into the feed tray 104 and to allow the fluid in the feed tray 104 to flow so that no dead spots occur, As shown, the baffle(s) 100 do not touch the sidewalls of the tray 104. They may if desired. Preferably when they do touch the sidewalls, there are one or more through holes formed in the baffle, preferably along its lower edge to allow for unimpeded fluid movement along the walls.

The height of the one or more baffles 100 is not critical so long as it is sufficient to help reduce the amount of movement of the liquid in the feed tray 104 while being handled. Typically, one can have the baffle height between 20% and 100% of the depth of the liquid in the tray 104. In another embodiment the baffle(s) height is between 35% and 80% of the depth of the liquid in the tray 104. Alternatively, the baffle(s) height is between 50% and 75% of the depth of the liquid in the tray 104.

The number of baffles is not critical. In one embodiment, it is preferred that only one baffle, either running at least partially the length or the width of the tray be used. In another embodiment, it is preferred that at least two baffles, at some defined cross direction to each other, be used. In such an embodiment, the two baffle(s) may be from about 25 degrees to 90 degrees to the direction of the other so as to ensure that the liquid movement is controlled in both the tray length and tray width directions.

Figure 5A:
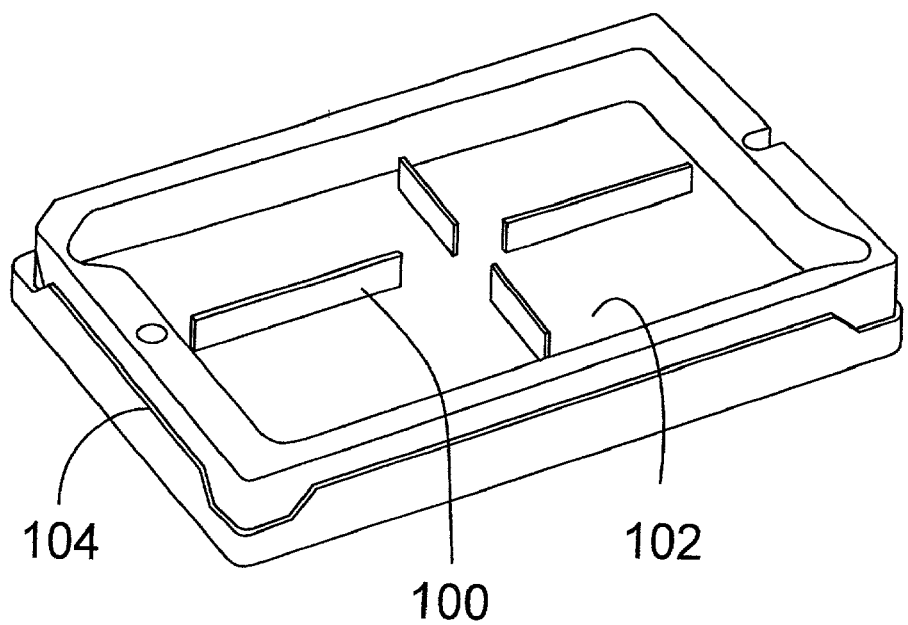
FIGS. 5A-D are a top down view of various alternative arrangements of the embodiment of FIG. 4.
Figure 5B:
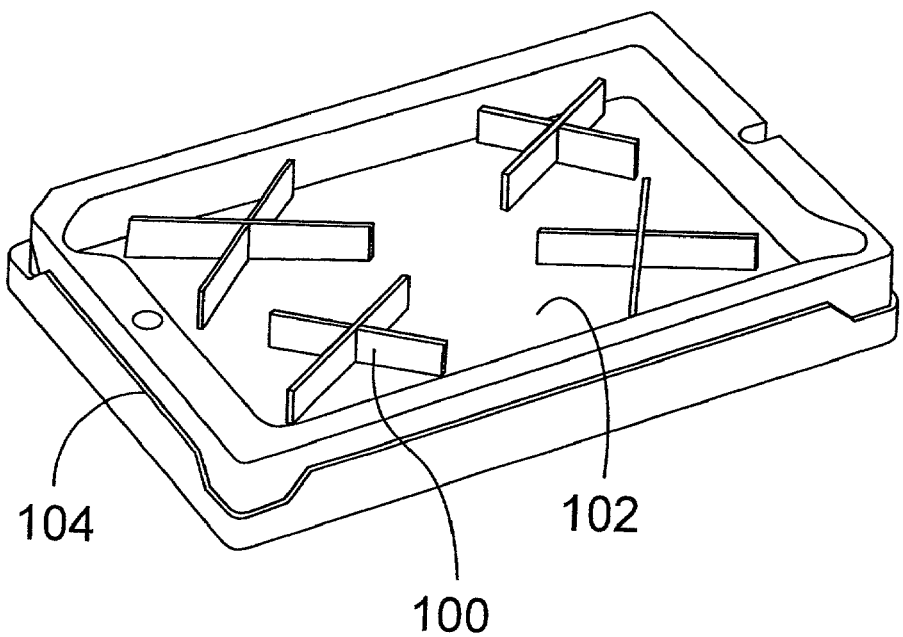
Figure 5C:
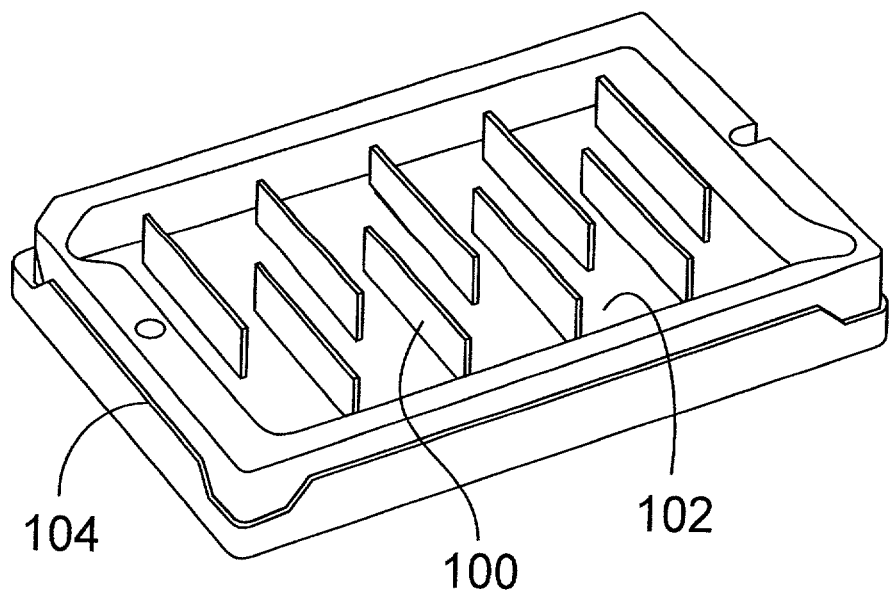
Figure 5D:
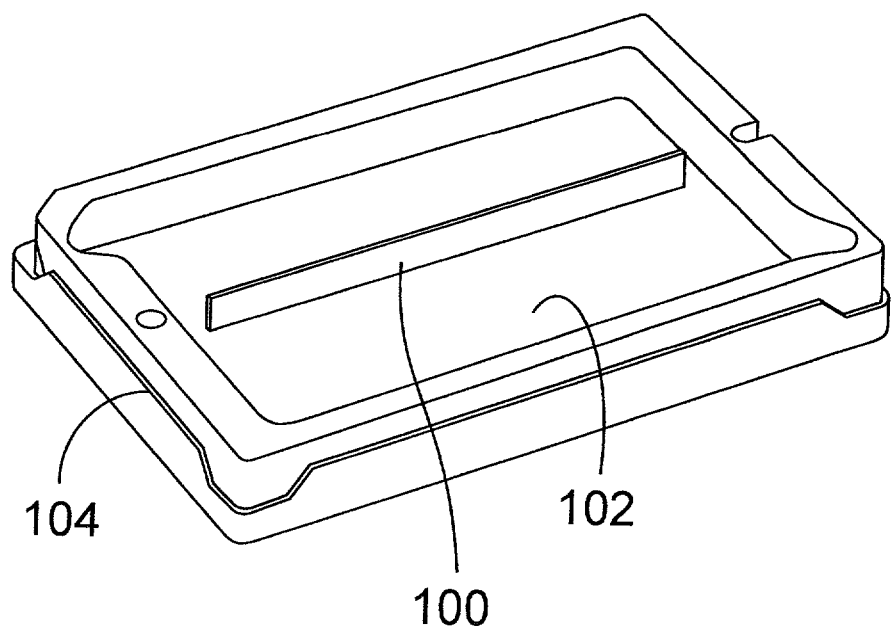

FIG. 5A shows an alternative arrangement of baffles in the embodiment of FIG. 7. In this Figure, straight baffles 100 are used instead of the wavy baffle design of FIG. 7. In FIG. 8B, the use of a series of repetitive baffles 100 is shown. Here, the baffles are shown as a series of "X" patterns spread across the feed tray bottom. FIG. 8C shows the use of a series of baffles 100 arranged in parallel and spaced part relationship to each other and each other baffle 100 extends out from the same side wall. In FIG. 8D is shown a single baffle that extend substantially the length of the feed tray.

Those baffles 100 may if desired have one or more through holes in them adjacent their bottom surface with the tray so as to allow for unimpeded flow through out the tray. Alternatively, in those baffles that are separately formed, the baffles are made such that they only touch the tray bottom at two or more points so that fluid may flow under the baffle(s).

In another embodiment, the baffle(s) may be used in lieu of the posts or protrusions discussed above as the means for allowing one to remove excess liquid from the bottom of the cell plate during its removal from the feed tray. In this embodiment (not shown), the baffle(s) should be of a height similar to that of the post or protrusions discussed above. Further, the number of baffles used should sufficient to ensure that all wells of the cell plate receive sufficient force so as to knock off any droplets without disturbing the cells growing in the plate.

What we claim is:

1. A multiwell test apparatus which comprises a feeding tray and a multiwell filter plate supported by said feeding tray, said multiwell filter plate comprising a multiplicity of wells extending from a plate, each of said wells comprising (a) a hollow member having two openings, one opening extending from said plate and (b) a permeable barrier secured about said opening extending from the plate, the barrier of said wells positioned within a void volume of said feeding tray, said feeding tray comprising a support surface, walls surrounding said surface to enclose said surface, a multiplicity of protrusions extending from said support surface in a direction substantially the same as a direction said walls extend from said support surface, said protrusions being located adjacent from 1 to 4 of the wells of the filter plate and further comprising one or more baffles on the support surface and the one or more baffles do not touch the walls of the feeding tray.

2. A multiwell test apparatus which comprises a feeding tray and a multiwell filter plate supported by said feeding tray, said multiwell filter plate comprising a multiplicity of wells extending from a plate, each of said wells comprising (a) a hollow member having two openings, one opening extending from said plate and (b) a permeable barrier secured about said opening extending from the plate, the barrier of said wells positioned within a void volume of said feeding tray, said feeding tray comprising a support surface, walls surrounding said surface to enclose said surface, a multiplicity of protrusions extending from said support surface in a direction substantially the same as a direction said walls extend from said support surface, said protrusions being located adjacent from 1 to 4 of the wells of the filter plate and further comprising one or more baffles on the support surface and the one or more baffles do not touch the walls of the feeding tray and two or more recesses formed in the walls of the feeding tray and two or more alignment posts formed in the filter plate which interact with the two or more recesses of the feeding tray walls.

* * * * *